United States Patent
Rao et al.

(10) Patent No.: US 11,147,956 B2
(45) Date of Patent: Oct. 19, 2021

(54) ENTERAL SYRINGE WITH VENTED COLLAR

(71) Applicant: Becton, Dickinson and Company, Franklin Lakes, NJ (US)

(72) Inventors: Milind Rao, Maywood, NJ (US); Lokesh Ramamurthy, Chennai (IN); Thirumurugan Nagu, Ramanathapuram (IN); Thomas Fraites, Ringwood, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 397 days.

(21) Appl. No.: 16/014,621

(22) Filed: Jun. 21, 2018

(65) Prior Publication Data

US 2019/0388671 A1    Dec. 26, 2019

(51) Int. Cl.
*A61M 39/10* (2006.01)
*A61J 15/00* (2006.01)
*A61J 1/20* (2006.01)

(52) U.S. Cl.
CPC ............ *A61M 39/10* (2013.01); *A61J 1/2096* (2013.01); *A61J 15/0076* (2015.05); *A61J 15/0096* (2013.01); *A61M 2039/1038* (2013.01); *A61M 2039/1094* (2013.01)

(58) Field of Classification Search
CPC .......... A61M 39/10; A61M 2039/1033; A61M 2039/1038; A61M 2039/1094; A61M 2039/0036; A61M 2202/0482; A61M 5/178; A61M 2005/3123; A61J 15/0076; A61J 15/0096; A61J 1/2096
See application file for complete search history.

(56) References Cited

U.S. PATENT DOCUMENTS

| | | |
|---|---|---|
| 4,390,017 A | 6/1983 | Harrison et al. |
| 5,609,584 A | 3/1997 | Gettig et al. |
| 6,183,421 B1 | 2/2001 | Bobo |
| 6,500,153 B1 | 12/2002 | Sheppard et al. |
| 6,599,269 B1 | 7/2003 | Lewandowski et al. |
| 7,066,914 B2 | 6/2006 | Andersen |
| 7,955,317 B2 | 6/2011 | Fournie |
| 8,292,875 B2 | 10/2012 | Kennard |
| D710,499 S | 8/2014 | Kawamura |
| D711,530 S | 8/2014 | Gleason, Jr. et al. |

(Continued)

FOREIGN PATENT DOCUMENTS

| | | |
|---|---|---|
| EP | 2583715 A1 | 4/2013 |
| JP | 2014514051 A | 6/2014 |

(Continued)

OTHER PUBLICATIONS

PCT International Search Report and Written Opinion in PCT/US2017/055023 dated Dec. 19, 2017, 16 pages.

(Continued)

*Primary Examiner* — Bhisma Mehta
*Assistant Examiner* — John J Crawford
(74) *Attorney, Agent, or Firm* — Servilla Whitney LLC (57) ABSTRACT

A syringe having an enteral collar with a vent is disclosed. The syringe may also include a plug which reversibly covers the vent. Other embodiments relate to the use of the syringe. The vent allows fluid within the region between the enteral collar and the tip to be removed.

19 Claims, 8 Drawing Sheets

(56) References Cited

U.S. PATENT DOCUMENTS

| | | |
|---|---|---|
| D714,935 S | 10/2014 | Nishioka et al. |
| 8,888,758 B2 | 11/2014 | Mansour et al. |
| D765,837 S | 9/2016 | Lev et al. |
| D767,124 S | 9/2016 | Lev et al. |
| D785,162 S | 4/2017 | Swisher et al. |
| 9,656,022 B1 | 5/2017 | Russo |
| D861,161 S | 9/2019 | Schuessler |
| 2006/0047251 A1 | 3/2006 | Bickford Smith et al. |
| 2008/0140020 A1* | 6/2008 | Shirley ............... A61J 15/0026 604/240 |
| 2010/0022966 A1 | 1/2010 | Kennard |
| 2010/0057004 A1* | 3/2010 | Christensen ...... A61M 25/0606 604/122 |
| 2011/0046568 A1 | 2/2011 | Enns |
| 2012/0022457 A1 | 1/2012 | Silver |
| 2012/0078214 A1 | 3/2012 | Finke et al. |
| 2012/0150129 A1 | 6/2012 | Jin et al. |
| 2013/0030379 A1 | 1/2013 | Ingram et al. |
| 2013/0090606 A1 | 4/2013 | Shams |
| 2013/0158560 A1 | 6/2013 | Gleason et al. |
| 2013/0226100 A1 | 6/2013 | Lev |
| 2013/0237904 A1 | 9/2013 | Deneburg et al. |
| 2013/0270819 A1 | 10/2013 | Amborn et al. |
| 2016/0067471 A1* | 3/2016 | Ingram ................. A61M 39/20 604/533 |
| 2016/0106928 A1 | 4/2016 | Davis et al. |
| 2016/0159635 A1* | 6/2016 | Davis ................... B67D 3/0041 141/366 |
| 2016/0279032 A1* | 9/2016 | Davis .................... A61M 5/142 |
| 2017/0021155 A1* | 1/2017 | Fruenlund ............ A61M 39/10 |
| 2017/0173321 A1 | 6/2017 | Davis et al. |
| 2017/0319438 A1* | 11/2017 | Davis ................. A61M 39/1011 |
| 2019/0030312 A1* | 1/2019 | Davis ................. A61J 15/0084 |

FOREIGN PATENT DOCUMENTS

| | | |
|---|---|---|
| WO | 2012134513 A1 | 10/2012 |
| WO | 2015146831 A1 | 10/2015 |
| WO | 2018067629 A1 | 4/2018 |
| WO | 2018067929 A1 | 4/2018 |

OTHER PUBLICATIONS

Non-Final Office Action in U.S. Appl. No. 29/695,580 dated Oct. 4, 2019, 8 pages.

PCT International Search Report and Written Opinion in PCT/US2019/038404 dated Sep. 9, 2019, 14 pages.

Non-Final Office Action in U.S. Appl. No. 29/695,580 dated Apr. 10, 2020, 8 pages.

* cited by examiner

ENTERAL SYRINGE WITH VENTED COLLAR

TECHNICAL FIELD

Aspects of the present disclosure relate to a syringe with an enteral connection feature and vents that allow the removal of fluid within the connection feature.

BACKGROUND

Enteral nutrition involves delivery of nutrient formula or medicine to the gastrointestinal tract. Administration of nutrients to a patient can be accomplished with an enteral feeding system, assembly or device. Enteral feeding systems typically utilize catheters inserted into a patient's nose or mouth, through which nutrients are administered to the gastrointestinal tract. A syringe or another device may be connected to the catheter to deliver the nutrients through the catheter. Nutrients and food may also be directly administered to a patient's mouth by a syringe, which may be referred to as an "oral syringe" or "oral delivery" of medication and does not require connection to a catheter or other device. Intravenous catheters are inserted into the vasculature of patients to effect intravascular treatment, which delivers medication through the circulatory or cardiovascular system by accessing any blood vessel. Such catheters include intravenous (IV) catheters, which are inserted into veins, and intra-arterial catheters, which are inserted into arteries.

Syringes are used to deliver fluids for a variety of medical applications, including, for example, oral delivery of nutrients, storage and delivery of fluid to enteral systems by connecting the syringe to an enteral connection, and intravenous delivery of fluids or medication. Delivery of medication through intravenous syringes involves connecting the distal end of a syringe to a catheter by a luer connection. A standard luer tip or standard luer connector has specifications as provided by the International Organization for Standardization (ISO) defined in ISO 80369-7:2016, including a 6% taper between the distal end and the proximal end. A standard male luer connector increases from the open distal end to the proximal end. A standard female luer connector decreases from the open proximal end to the distal end. According to ISO 80369-7:2016, a standard male luer connector has an outer cross-sectional diameter measured 0.75 mm from the distal end of the tip of between 3.970 mm and 4.072 mm. The length of the standard male luer taper is between 7.500 mm to 10.500 mm. The outer cross-sectional diameter measured 7.500 mm from the distal end of the tip is between 4.376 mm and 4.476 mm. As used herein, the phrases "standard male luer connector" and "standard female luer connector" shall refer to connectors having the dimensions described in ISO 80369-7, which is hereby incorporated by reference in its entirety.

Delivery of enteral fluid such as breast milk or formula from a syringe having a barrel and a plunger in the barrel is achieved by advancing the plunger into the barrel to pressurize the fluid within the barrel and discharge the fluid from the distal tip of the syringe. Oral dose syringes have a barrel with distal tip defining a channel having a diameter substantially larger than the diameter of a needle cannula. For a typical oral syringe, the distal tip defines a smooth exterior surface that is insertable into the mouth of a patient to orally introduce medication or other fluids into a patient.

Limiting the use of standard luer tips and connectors to use with vascular access systems is one consensus accepted by device manufacturers and regulatory bodies. Recently, the International Standards Organization promulgated ISO 80369-3, which is hereby incorporated by reference in its entirety, to define a safe design for an enteral feeding connector, which is also referred to as ENFit connector. The new ENFit connector has a unique enteral-specific design that provides a simple way to reduce the risk of enteral tube feeding misconnections and improve patient safety. This enteral-specific design has an enteral collar that surrounds a non-luer tip, the enteral collar including threaded area around the tip of the connector. This area of the collar is sometimes referred to as a moat.

One method of using an enteral syringe is to fill the syringe with a fluid medication from a cup by inserting the syringe into the cup and drawing up the medication. This method may be referred to as a "cup fill" operation. During this operation, there is the possibility that the volume of the moat is filled (partially or completely) with the medication. A medical practitioner performing the cup fill operation may remove medication from the moat by flicking the syringe barrel with a finger or tapping the syringe barrel, however, it is difficult to ensure that the entire moat has been cleared of medication.

Residual medication left in the moat is undesirable for several reasons. First, any residual medication in the moat may interfere when other components (e.g., feeding tubes, extension sets, etc.) are connected to the syringe. Also, any residual medication may lead to dose accuracy issues (typically overdose), thereby potentially affecting patient safety. Therefore, there is a need for a syringe design which allows for emptying the moat of any medication.

SUMMARY

A first embodiment of the present disclosure pertains to a syringe comprising a syringe barrel having a distal end, an open proximal end, and a sidewall extending between the distal end to the open proximal end. The sidewall defines a chamber. The syringe comprises a non-luer tip at the distal end of the syringe barrel. The non-luer tip dimensioned such that the non-luer tip is not connectable to an intravenous device. The non-luer tip defines a fluid pathway in fluid communication with the chamber. The syringe comprises an enteral collar having a distal end and a proximal end. The proximal end includes a rim circumferentially abutting the distal end of the syringe barrel. The enteral collar surrounds at least a portion of the non-luer tip. The enteral collar is sized to permit connection to an enteral device and prevent connection to a device having a standard luer connector. The enteral collar comprises a vent at the proximal end.

In another embodiment, a syringe comprises a syringe barrel having a distal end, an open proximal end, and a sidewall extending between the distal end to the open proximal end. The sidewall defines a chamber. The syringe comprises a non-luer tip at the distal end of the syringe barrel. The non-luer tip dimensioned such that the non-luer tip is not connectable to an intravenous device. The non-luer tip defines a fluid pathway in fluid communication with the chamber. The syringe comprises an enteral collar having a distal end and a proximal end. The proximal end includes a rim circumferentially abutting the distal end of the syringe barrel. The distal end of the enteral collar has an inner surface with threads for engaging a threaded, non-luer connector. The enteral collar surrounds at least a portion of the non-luer tip which extends beyond the proximal end of the enteral collar. The enteral collar is sized to permit connection to an enteral device and prevent connection to a device having a standard luer connector. The enteral collar comprises four vents at the proximal end. The vents are equally spaced around a circumference of the enteral collar and configured to allow for removal of fluid between the enteral collar and the non-luer tip.

A further aspect of the present disclosure pertains to a method of adding fluid to a syringe. According to an embodiment of the method, the syringe to which fluid is added comprises a syringe barrel having a distal end, an open proximal end and a sidewall extending between the distal end to the open proximal end, the sidewall defining a chamber. The syringe used according to the method further comprises a non-luer tip at the distal end of the syringe barrel, the non-luer tip dimensioned such that the non-luer tip is not connectable to an intravenous device, and the non-luer tip defines a fluid pathway in fluid communication with the chamber. The syringe further comprises a plunger within the chamber, an enteral collar having a distal end and a proximal end, the proximal end including a rim circumferentially abutting the distal end of the syringe barrel. The enteral collar surrounds at least a portion of the non-luer tip, the enteral collar sized to permit connection to an enteral device and prevent connection to a device having a standard luer connector and comprising a vent at the proximal end. According to an embodiment of the method, the distal end of the syringe barrel is placed in a liquid within a liquid reservoir, and the liquid is drawn into the syringe by displacing the plunger within the chamber.

DETAILED DESCRIPTION

Before describing several exemplary embodiments of the disclosure, it is to be understood that the disclosure is not limited to the details of construction or process steps set forth in the following description. The disclosure is capable of other embodiments and of being practiced or being carried out in various ways.

In this disclosure, a convention is followed wherein the distal end of the device is the end closest to a patient and away from a practitioner. Conversely, the proximal end of the device is the end away from the patient and closest to a practitioner.

The term "not connectable" with respect to male and female connectors refers to a connector having a shape, size, dimension or structure that prevents connection to another connector. For example, a female non-luer connector has a shape, size, dimension and/or structure that prevents it from forming a connection with standard a male luer connector and is thus not connectable with respect to the standard male luer connector. Such a female non-luer connector, however, has a shape, size, dimension and/or structure that permits formation of a connection with a male non-luer connector and is, thus, connectable with respect to the male non-luer connector.

As used herein, the term "dimension" shall include the length, diameter or width of a geometric shape or the geometrically shaped components described herein. The term "cross-sectional diameter" shall include the measurement of the longest distance or greatest distance between two points on an edge of a cross-section of an object or component with a circular or non-circular cross-section.

The two points may be located on the inside surface or outside surface of the edge of the cross-section of the object. The cross-sectional diameter of two points located on the inside surface of the edge of the cross-section of the object shall be referred to as the "inside cross-sectional diameter" and the cross-sectional diameter of two points located on the outside surface of the edge of the cross-section of an object shall be referred to as the "outside cross-sectional diameter." It should be recognized that "cross-sectional diameter" of objects having a circular cross-section may be referred to as the "cross-sectional dimension" or "diameter" of the object. The terms "cross-sectional dimension," "cross-sectional diameter" and "diameter" may be used interchangeably for objects having a circular cross-section.

One or more embodiments provide a syringe with an enteral collar that enables the syringe meet ISO 80369-3 misconnection requirements. In one or more embodiment, the enteral collar has a vent or gap in the enteral collar to allow for removal of fluid between the enteral collar and the syringe tip. In one or more embodiment, the enteral collar comprises more than one vent or gap. In one or more embodiment, the vent is placed so as to allow fluid to travel along a threaded region of the enteral collar and out of the collar. In one or more embodiment, the syringe comprises a plug that reversibly seals the vent. In some embodiments, the plug is removable or may be displaced along the longitudinal axis of the syringe barrel to open the vent. In some embodiments, the plug is rotatable and comprises a gap which can be aligned with the vent to open the vent.

According to one or more embodiments, the syringe can be utilized to draw-up, fill and enterally administer medication or other fluids without fluid in the region between the enteral collar and the syringe tip. In one or more embodiment, the syringe can be agitated after drawing-up or filling the syringe to ensure that fluid between the enteral collar and the syringe tip is removed through the vent.

One or more embodiments provide a syringe that can be connected to enteral feeding sets and feeding tubes. In the industry, the connection is referred to as ENFit and is compliant to ISO 80369-3. According to one or more embodiments, a syringe is provided that permits the syringe to be connected to enteral tubing and enteral devices such as feeding bags and prevents connection to non-enteral devices, such as intravenous lines, urinary catheters and ventilator tubing. One or more embodiments provide a syringe that is compliant with ENFit devices and ISO 80369-3 and the syringe is not be compatible with a standard luer connection, thus preventing misadministration of an enteral feeding or medication by the wrong route. Thus, a syringe is provided with a connector that has a unique enteral-specific design and provides a simple way to reduce the risk of enteral tube feeding misconnections and improve patient safety. Furthermore, the collar does not allow connectivity with any other connector for any other clinical use such as intravenous devices. According to one or more embodiments, the syringe provides an enteral-specific syringe that can be used to administer medicine, flush, hydrate, or bolus feed through ENFit feeding tubes and extension sets compliant with ISO 80369-3. One or more embodiment provides a syringe having an enteral collar that does not connect with standard luer connectors that are compliant with ISO Standard 80369-7. Thus, an embodiment of the disclosure provides a syringe having a connector with a dimension that is not compatible with standard sized intravenous connectors and ports, thereby keeping the two from being inadvertently mechanically coupled.

Aspects of the present disclosure pertain a syringe having an enteral collar with a female connector that prevents misconnection to non-compatible male connectors. A compatible connector shall be defined herein as a connector that has a shape, size, dimension or structure to another connector. Non-compatible male connectors may include standard male luer connectors, which conform to ISO 80369-7:2016.

Referring now to FIGS. 1-6, a first embodiment of a syringe 10 is shown. The syringe 10 includes a syringe barrel 12 having a distal end 14, an open proximal end 16, and a sidewall 18 extending between the distal end 14 to the open proximal end 16, the sidewall 18 defining a chamber 20. The axis from the distal end 14 to the open proximal end 16 being the longitudinal axis. The syringe further includes a non-luer tip 24 at the distal end 14 of the syringe barrel 12 dimensioned such that the non-luer tip 24 is not connectable to an intravenous device, the non-luer tip 24 defining a fluid pathway 26 in fluid communication with the chamber 20. The syringe 10 further comprises an enteral collar 30 having a distal end 32 and a proximal end 34. The proximal end 34 of the enteral collar 30 includes a rim 36 circumferentially abutting the distal end 14 of the syringe barrel 12. The enteral collar 30 surrounds at least a portion of the non-luer tip 24. The enteral collar 30 is sized to permit connection to an enteral device and prevent connection to a device having a standard luer connector. In the embodiment shown, the enteral collar 30 comprises a vent 50 at the proximal end 34 of the enteral collar 30.

Figure 5:
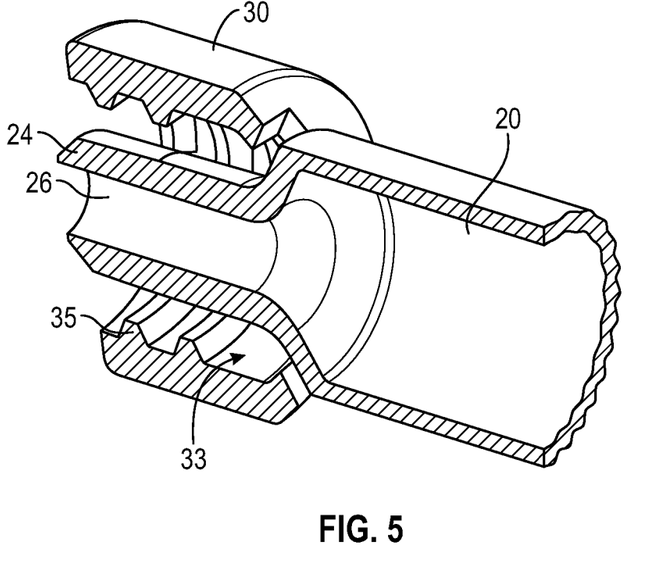
FIG. 5 is a cross-sectional view of the enteral collar shown in FIG. 4 taken along line B-B'.

As best shown in FIG. 5, in one or more embodiments, the enteral collar 30 is outside the fluid pathway 26 and not in fluid communication with the chamber 20. In other words, fluid contained in the chamber 20 of the syringe 10 flows through non-luer tip 24, and fluid flowing through the non-luer tip 24 is not in contact with the enteral collar 30.

Figure 6:
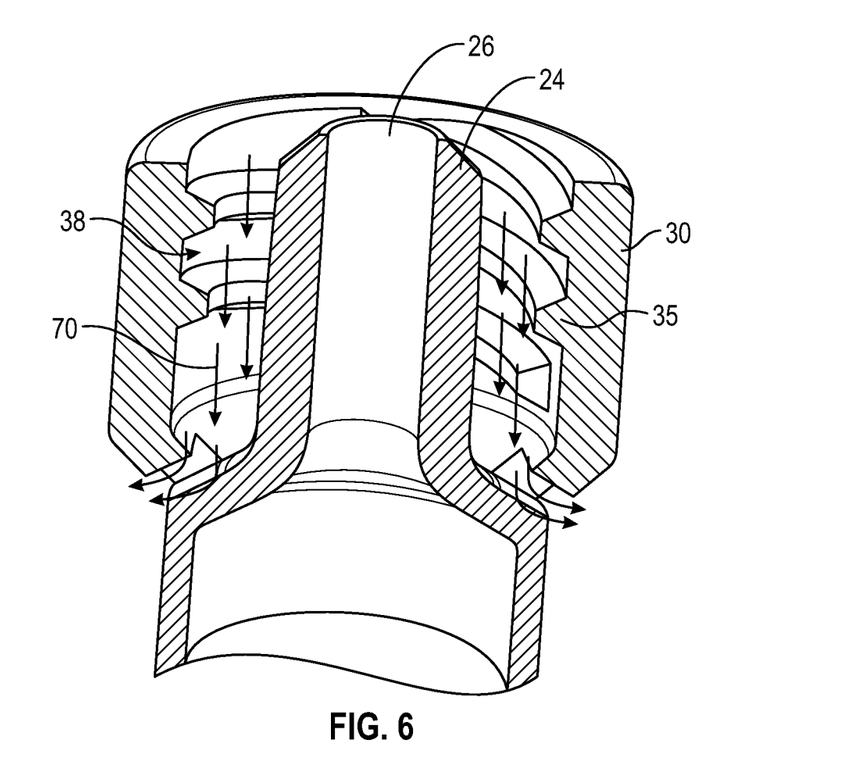
FIG. 6 is cross-sectional view of the enteral collar shown in FIG. 4 depicting the flow of fluid through the moat.
Figure 7:
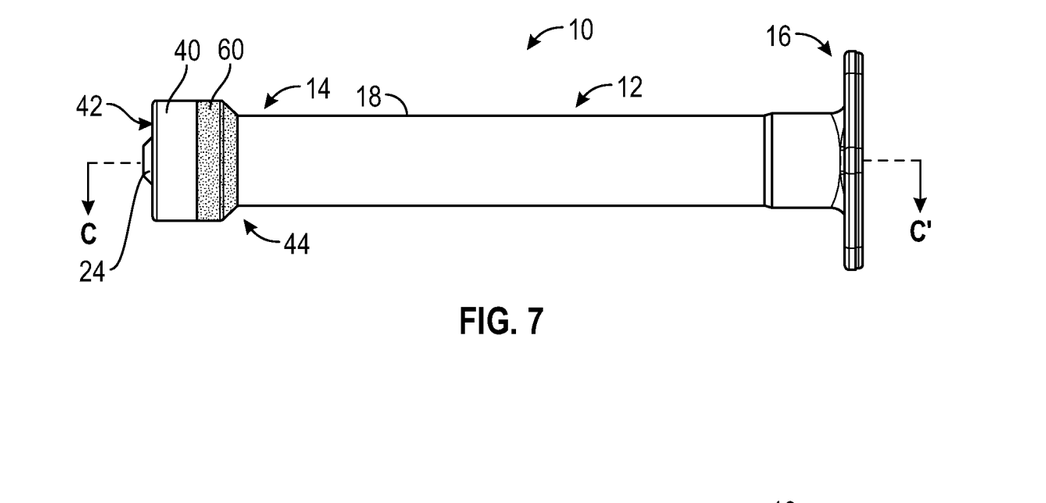
FIG. 7 is a side view of a syringe with a plug according to one embodiment.
Figure 8:
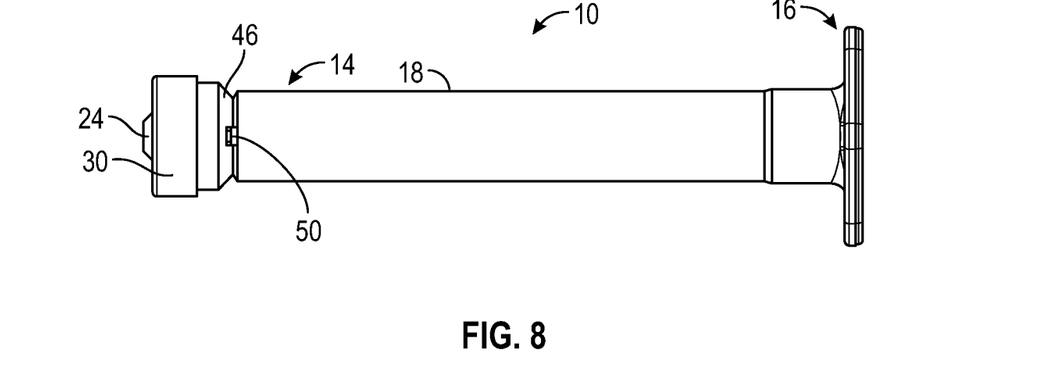
FIG. 8 is a side view of the syringe shown in FIG. 7 with the plug removed from the syringe.
Figure 9:
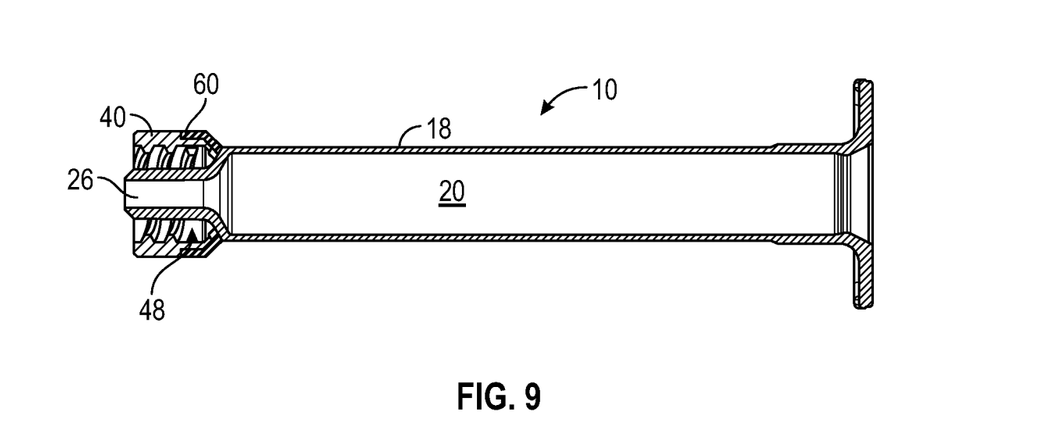
FIG. 9 is a cross-sectional view of the syringe shown in FIG. 7 taken along line C-C'.
Figure 10A:
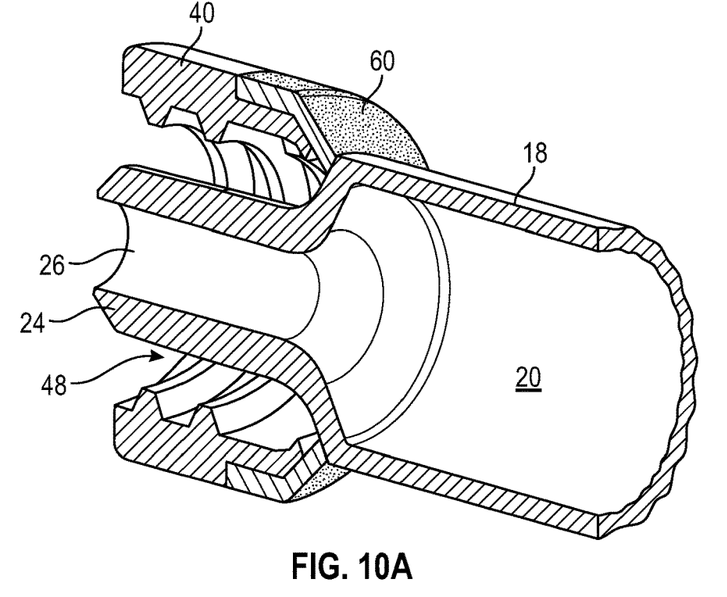
FIG. 10A is a cross-sectional perspective view of the enteral collar of the syringe shown in FIG. 7.
Figure 10B:
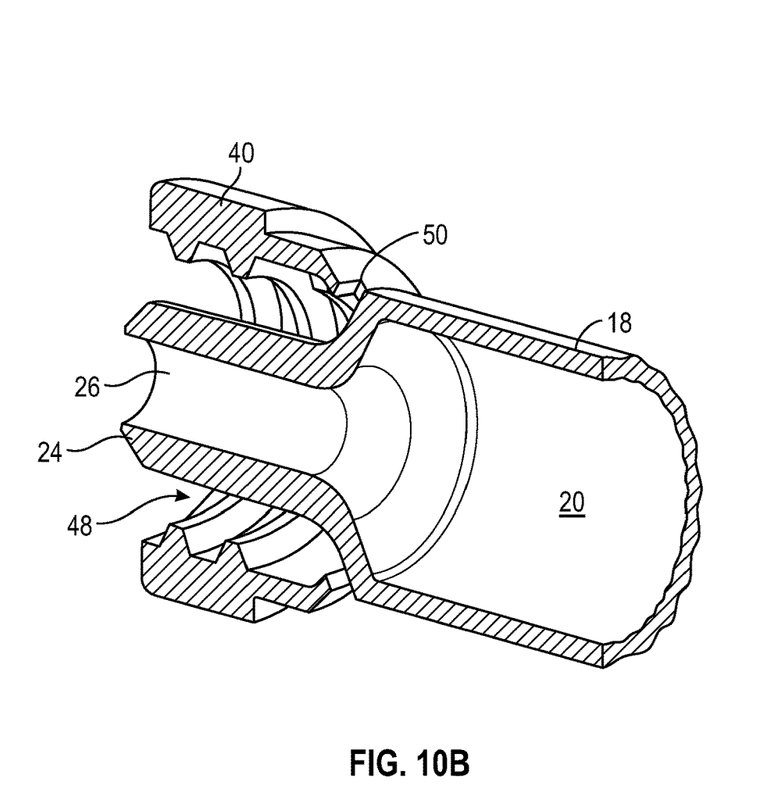
FIG. 10B is a cross-sectional perspective view of the enteral collar of the syringe shown in FIG. 8.

In some embodiments, the vent 50 is configured to provide an opportunity or means of escape, passage, or release of fluid between the enteral collar 30 and the non-luer tip 24. As shown in FIG. 6, the vent 50 may be configured to allow fluid to be removed by traveling according to the arrows 70 through a moat region 38 between the enteral collar 30 and the non-luer tip 24 and through the vent 50. Although not shown in the Figures, in some embodiments, the vent 50 is configured to allow for removal of fluid by air entering the vent 50 to relieve negative pressure and facilitate fluid traveling through the moat region 38 between the enteral collar 30 and the non-luer tip 24 opposite the direction shown in FIG. 6 (i.e. exiting near the distal end 32 of the enteral collar 30).

The vent may be any suitable shape through which a fluid may pass. In some embodiments, the vent is rectangular, square, diamond, oval or circular in shape. In some embodiments, the enteral collar 30 comprises a number of vents 50 in a range of from 1 to 12. In the embodiment shown, the enteral collar 30 comprises four vents 50 (three are visible in FIG. 3) at the proximal end 34 of the enteral collar 30. In some embodiments the vents have a rectangular shape, with an aspect ratio of length to width of the rectangle of about 2 to 1. In specific embodiments, the rectangular vents have a length×width dimensions in a range of from 1-5 mm length and 0.5-5 mm width, with an aspect ratio of length to width of about 2 to 1. In a specific embodiment, the length of a rectangular vent is 2 mm and the width is about 1 mm.

Figure 1:
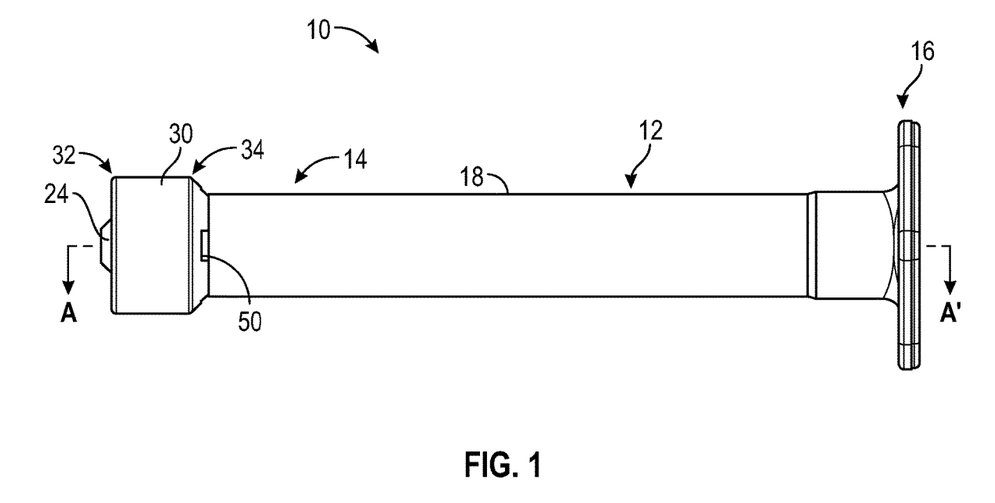
FIG. 1 is a side elevation view of a syringe according to one embodiment.
Figure 2:
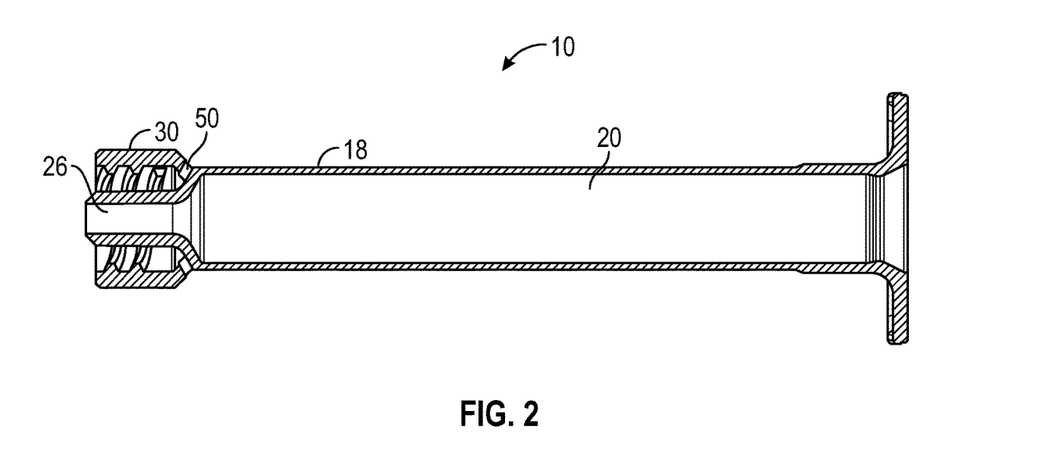
FIG. 2 is a cross-sectional view of the syringe shown in FIG. 1 taken along line A-A'.
Figure 3:
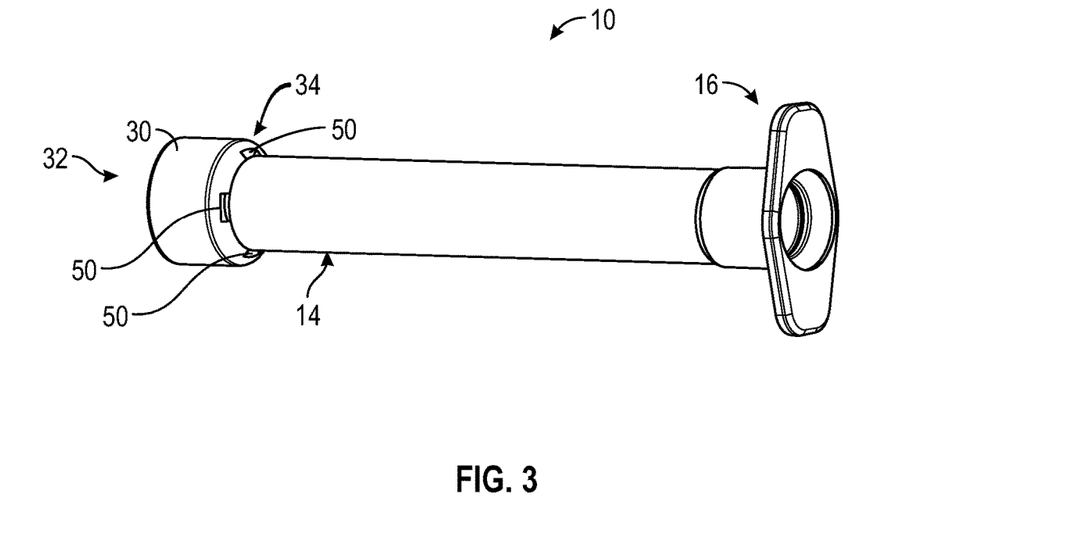
FIG. 3 is a perspective view from the proximal end of the syringe shown in FIG. 1.
Figure 4:
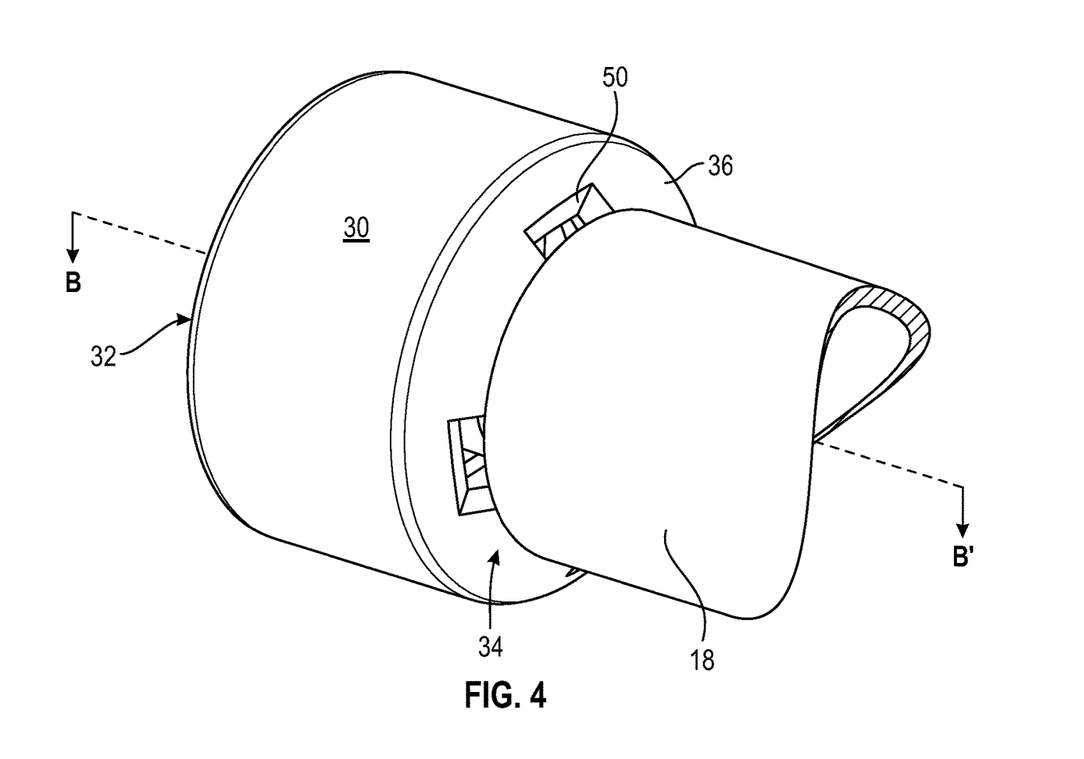
FIG. 4 is an enlarged partial perspective view of the enteral collar of the syringe shown in FIG. 1.

The vent 50 may be located in any suitable position on the enteral collar 30. In some embodiments, the vent 50 is located near the proximal end 34 of the enteral collar 30. In some embodiments, the vent 50 is located within the rim 36 of the enteral collar 30 which abuts the distal end 14 of the syringe barrel 12. As shown in FIG. 3, in some embodiments, the enteral collar 30 comprises a plurality of vents 50 equally spaced around the circumference of the enteral collar 30. For example, four vents 50 may be spaced approximately 90 degrees apart around the circumference of the enteral collar 30.

The proximal end 34 of the enteral collar 30 abuts the distal end 14 of the syringe barrel 12. In some embodiments, the enteral collar 30 is continuous with the sidewall 18. As used in this regard, "continuous" means that the enteral collar 30 and the sidewall 18 are formed from the same material without an intervening seam or other separation. In some embodiments, the enteral collar 30 is not removable from the syringe or rotatable relative to the syringe barrel 12.

The enteral collar 30 surrounds at least a portion of the non-luer tip 24. In embodiments similar to those pictured, the non-luer tip 24 extends beyond the distal end 32 of the enteral collar 30. In some non-illustrated embodiments, the distal end 32 of the enteral collar 30 extends beyond the end of the non-luer tip 24. In some embodiments, the non-luer tip is sized and dimensioned to provide an ENfit connection that conforms to ISO 80369-3 and is connectable with an opposite ENfit connector that also conforms to ISO 80369-3.

As shown in FIG. 5, in some embodiments, the enteral collar 30 has an inner surface 33 with internal threads 35 or a lug to provide a female non-luer connector, which can engage a male non-luer connector. While not pictured, in other embodiments, the enteral collar 30 has an external surface with external threads or lug to provide a male non-luer connector, which can engage a female non-luer connector. The threads or lug, whether internal or external, are configured to engage a threaded, non-luer connector. In some embodiments, the enteral collar 30 is configured to provide a connector that provides an ENfit connection that conforms to ISO 80369-3 and is connectable with an opposite ENfit connector that also conforms to ISO 80369-3.

Referring now to FIGS. 7-11B, a further embodiment of the syringe 10 is shown. Similar to the syringe of the first embodiment, the syringe 10 includes a syringe barrel 12 having a distal end 14, an open proximal end 16, a sidewall 18 extending between the distal end 14 to the open proximal end 16, the sidewall 18 defining a chamber 20. The axis from the distal end 14 to the open proximal end 16 defines a longitudinal axis. The syringe 10 includes a non-luer tip 24 dimensioned such that the non-luer tip 24 is not connectable to an intravenous device. The non-luer tip 24 defines a fluid pathway 26 in fluid communication with the chamber 20. The syringe 10 has an enteral collar 40 having a distal end 42 and a proximal end 44. The proximal end 44 of the enteral collar 40 includes a rim 46 circumferentially abutting the distal end 14 of the syringe barrel 12. The enteral collar 40 surrounds at least a portion of the non-luer tip 24. The enteral collar 40 is sized to permit connection to an enteral device and prevent connection to a device having a standard luer connector. The enteral collar 40 comprises a vent 50 at the proximal end 44 of the enteral collar 40.

The enteral collar 40 is similar to the enteral collar 30 except that the enteral collar 40 further comprises a plug 60 configured to reversibly seal the vent 50. In one or more embodiments, a plug configured to reversibly seal a vent is capable of being positioned so as to seal a vent or leave a vent unaffected and can be transitioned between the two positions.

Figure 11A:
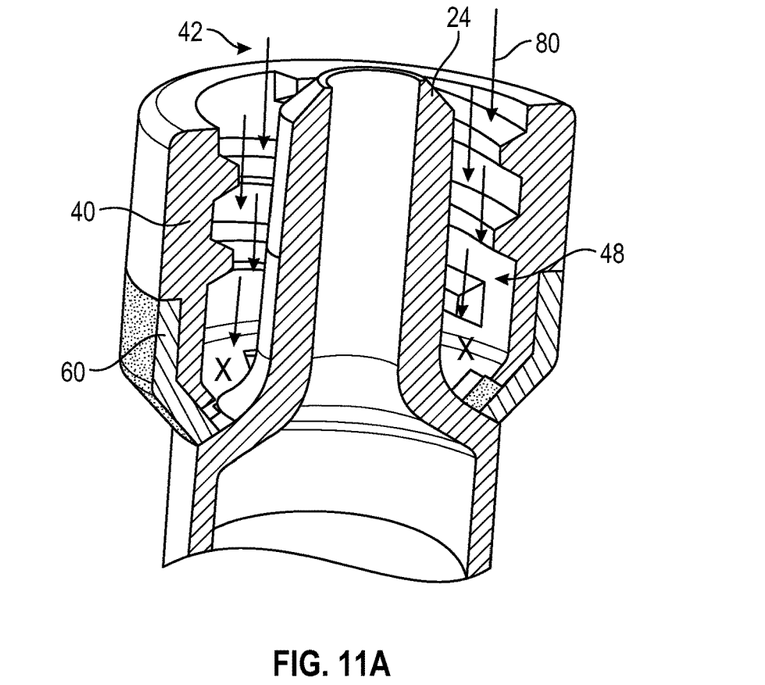
FIG. 11A is a cross-sectional view of the enteral collar of the syringe shown in FIG. 7 depicting the flow of fluid through the moat.

The position in which the plug seals the vent is described as "closed." As illustrated in FIG. 11A, when closed, fluid within the moat region 48 between the enteral collar 40 and the non-luer tip 24 may travel according to the arrows 80 but will not be able to be removed through the vent 50. Similarly, the plug 60 would prevent air from entering the vent 50 to relieve negative pressure, thereby preventing flow of fluid through the moat region 48 in the opposite direction from that shown by the arrows 80 in FIG. 11A.

Figure 11B:
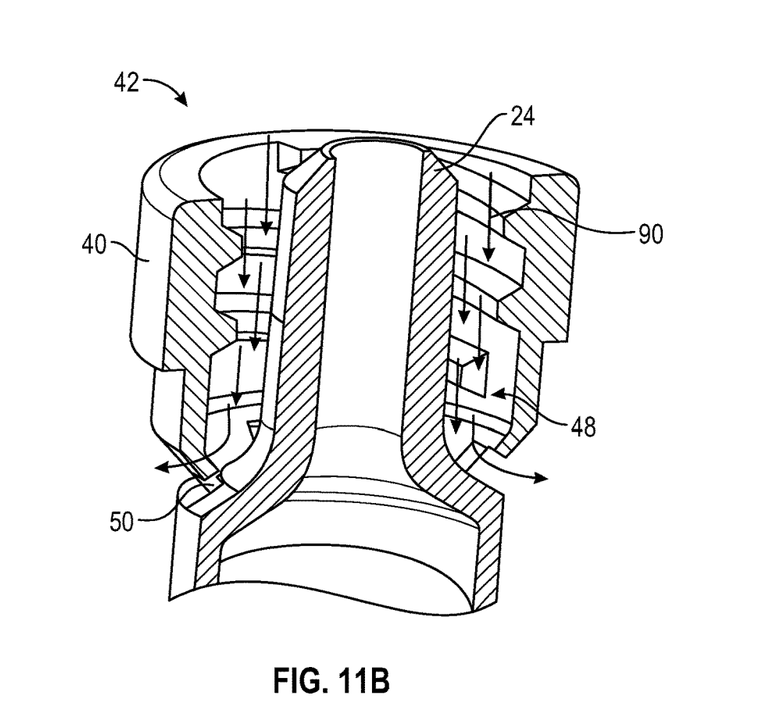
FIG. 11B is a cross-sectional view of the enteral collar of the syringe shown in FIG. 8 depicting the flow of fluid through the moat.

Conversely, when the plug does not seal the vent, the position is described as "open". As illustrated in FIG. 11B, when open, fluid within the moat region 48 between the enteral collar 40 and the non-luer tip 24 may travel according to the arrows 90 and will be able to be removed through the vent 50. Similarly, the plug 60 will allow air to enter the vent 50 so as to relieve negative pressure in the moat region 48, thereby allowing the flow of fluid through the moat region 48 in the opposite direction from that shown by the arrows 90 in FIG. 11B.

Several methods of transitioning the plug from a position where the vent is sealed to a position where the vent is unsealed are envisioned. In some embodiments, the plug 60 is removable from the syringe 10. After removal, the syringe 10 may appear as in FIG. 8, 10B or 11B. In some embodiments, the plug 60 can be displaced along the longitudinal axis of the syringe barrel 12. The plug 60 may be displaced proximally, towards the practitioner, on the syringe barrel 12 or distally, away from the practitioner, on the enteral collar 40.

In a specific embodiment, the plug 60 is rotatable and comprises a gap which can be aligned with the vent 50. In some embodiments, the plug 60 comprises a number of gaps equal to the number of vents 50 in the enteral collar 40. In some embodiments, the plug 60 comprises more gaps than the number of vents 50 in the enteral collar 40. In some embodiments, the plug 60 comprises fewer gaps than the number of vents 50 in the enteral collar 40. In some embodiments, the gap has an area greater than or equal to the area of the vent 50.

Another embodiment of the disclosure relates to a method for using a syringe described according to one or more embodiments herein. In particular, the method comprises adding fluid to the syringe. According to some embodiments of the method, the syringe comprises a plunger within the chamber. The non-luer tip is placed in fluid communication with a liquid within a liquid reservoir. The plunger is displaced within the chamber to draw the liquid into the syringe.

The syringe provided may be a syringe comprising an enteral collar 30 or an enteral collar 40. Accordingly, the syringe may comprise a plug 60. If present, the plug 60 may be positioned in an open position or a closed position.

Placing the non-luer tip in fluid communication with the liquid may be implemented in a variety of ways. In some embodiments, the tip is placed directly in a liquid within a liquid reservoir. In some embodiments, the tip may be connected to the proximal end of a medication straw which has a distal end within the liquid. In some embodiments, the tip may be connected to a bottle fill cap and the bottle inverted to place the tip in fluid communication with the liquid inside the bottle. Regardless of the method used, when the plunger is displaced within the chamber, the liquid is drawn into the syringe.

The liquid may be any suitable liquid. In some embodiments, the liquid is a liquid medication. In some embodiments, the liquid is a nutritional supplement and/or dietary supplement.

Figure 12:
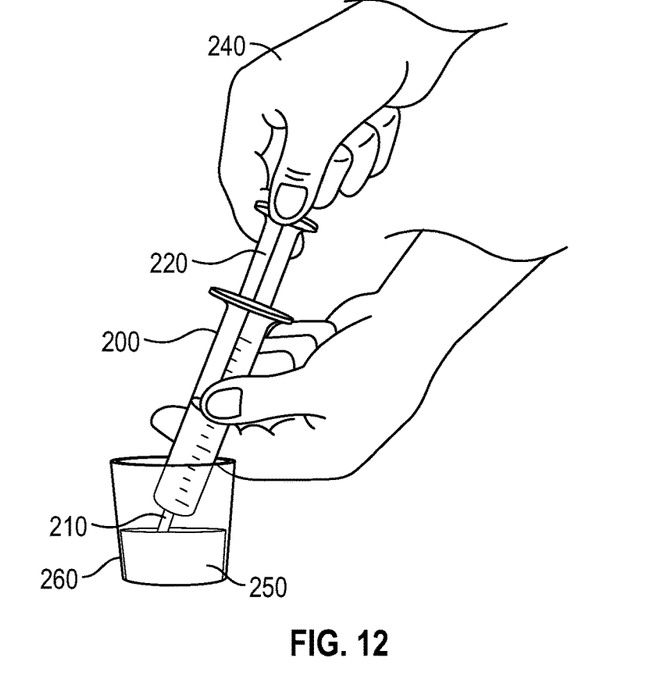
FIG. 12 is an illustration of a syringe during a cup fill operation.

In specific embodiments, the method comprises a "cup-fill" method. In general, as illustrated in FIG. 12, a cup-fill method comprises placing the tip 210 of a syringe 200 in a liquid 250 within a liquid reservoir 260. The practitioner 240 draws back the plunger 220 of the syringe 200 in order to fill the syringe 200 with the liquid 250.

Figure 13:
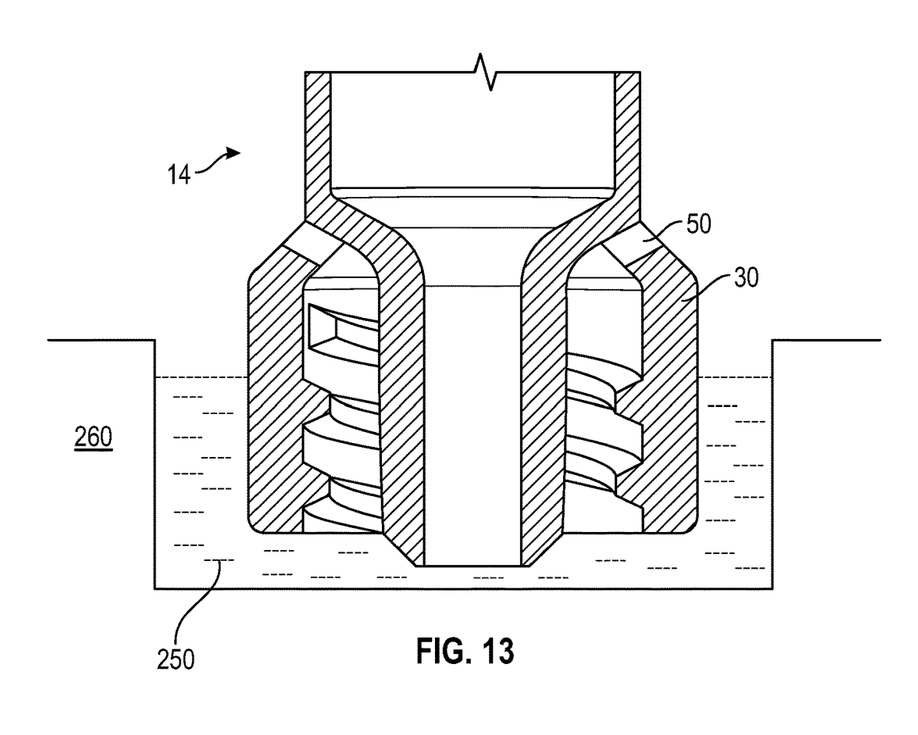
FIG. 13 is a cross-sectional view of the enteral collar of FIG. 4 within a liquid reservoir according to one embodiment.

As illustrated in FIG. 13, a syringe 10 with an enteral collar 30 may be placed in a liquid 250 within a liquid reservoir 260. Once placed into the liquid 250, the moat region 38 is filled with liquid 250 to the level of the liquid 250 in the liquid reservoir 260. In some embodiments, the syringe 10 is placed in the liquid 250 such that the vent 50 is above the level of the liquid 250 within the liquid reservoir 260. The liquid 250 is drawn into the syringe 10 by displacing the plunger.

After drawing the liquid 250 into the syringe 10, the syringe 10 is removed from the liquid 250. When removed, the vent 50 allows for the liquid 250 to flow out of the moat region 38. The liquid 250 may flow through the vent 50 or out through the distal end 32 of the enteral collar 30. In some embodiments, the method further comprises agitating the syringe 10 to ensure that liquid 250 in the moat region 38 is removed. Agitating the syringe may include, without limitation, tapping or flicking the syringe 10.

In some embodiments, the syringe 10 comprises an enteral collar 40 with a plug 60. In some embodiments, the vent 50 is sealed by the plug 60 (i.e. closed) when the syringe 10 is placed in the liquid 250 and then unsealed (i.e. open) after drawing the liquid into the syringe. In some embodiments, the plug 60 is rotated to unseal the vent 50. In some embodiments, the plug 60 is removed to unseal the vent 50.

Without being bound by theory, it is believed that if the vent is closed during a cup-fill method, the positive pressure within the moat region will minimize the amount of liquid therein. Once filled, opening the vent will allow liquid which accumulates in the moat region to be removed.

The components of the syringe including the enteral collar, plug and plunger may be fabricated of a variety of materials suitable for medical and health care applications, such as, but not limited to, nylon, polypropylene, polycarbonate, polyvinylidene fluoride, acrylonitrile butadiene styrene, and polyvinyl chloride. In some embodiments, the plug and the plunger are fabricated from the same material.

Reference throughout this specification to "one embodiment," "certain embodiments," "one or more embodiments" or "an embodiment" means that a particular feature, structure, material, or characteristic described in connection with the embodiment is included in at least one embodiment of the disclosure. Thus, the appearances of the phrases such as "in one or more embodiments," "in certain embodiments," "in one embodiment" or "in an embodiment" in various places throughout this specification are not necessarily referring to the same embodiment of the disclosure. Furthermore, the particular features, structures, materials, or characteristics may be combined in any suitable manner in one or more embodiments.

Although the disclosure herein has been described with reference to particular embodiments, it is to be understood that these embodiments are merely illustrative of the principles and applications of the present disclosure. It will be apparent to those skilled in the art that various modifications and variations can be made to the method and apparatus of the present disclosure without departing from the spirit and scope of the disclosure. Thus, it is intended that the present disclosure include modifications and variations that are within the scope of the appended claims and their equivalents.

What is claimed is:

1. A syringe comprising:
    a syringe barrel having a distal end, an open proximal end, a sidewall extending between the distal end to the open proximal end, and the sidewall defining a chamber;
    a non-luer tip at the distal end of the syringe barrel and dimensioned such that the non-luer tip is not connectable to an intravenous device, the non-luer tip defining a fluid pathway in fluid communication with the chamber;
    an enteral collar having a distal end and a proximal end, the proximal end including a rim circumferentially abutting the distal end of the syringe barrel, the enteral collar surrounding at least a portion of the non-luer tip and defining a moat region around the non-luer tip, the enteral collar sized and configured to permit a threaded connection of the distal end of the enteral collar to an enteral device and prevent connection to a device having a standard luer connector, the proximal end of the enteral collar comprising a vent configured to allow removal of fluid from the moat region; and
    a plug that reversibly seals the vent and that can be displaced along a longitudinal axis of the syringe barrel.

2. The syringe of claim 1, wherein the vent is configured to allow for removal of fluid between the enteral collar and the non-luer tip.

3. The syringe of claim 1, wherein the vent is rectangular, square, diamond, oval, or circular.

4. The syringe of claim 1, wherein the enteral collar comprises a number of vents in a range of from 4 to 12.

5. The syringe of claim 1, wherein the enteral collar comprises a plurality of vents equally spaced around a circumference of the enteral collar.

6. The syringe of claim 1, wherein the plug is removable.

7. The syringe of claim 1, wherein the enteral collar is outside the fluid pathway and not in fluid communication with the chamber.

8. The syringe of claim 1, wherein the distal end of the enteral collar has an inner surface with threads for engaging a threaded, non-luer connector.

9. The syringe of claim 1, wherein the enteral collar is not removable or rotatable relative to the syringe barrel.

10. The syringe of claim 1, wherein the non-luer tip extends beyond the distal end of the enteral collar.

11. A syringe comprising:
    a syringe barrel having a distal end, an open proximal end, a sidewall extending between the distal end to the open proximal end, and the sidewall defining a chamber;
    a non-luer tip at the distal end of the syringe barrel and dimensioned such that the non-luer tip is not connectable to an intravenous device, the non-luer tip defining a fluid pathway in fluid communication with the chamber;
    an enteral collar having a distal end and a proximal end, the proximal end including a rim circumferentially abutting the distal end of the syringe barrel, the enteral collar surrounding at least a portion of the non-luer tip and defining a moat region around the non-luer tip, the enteral collar sized and configured to permit a threaded connection of the distal end of the enteral collar to an enteral device and prevent connection to a device having a standard luer connector, the proximal end of the enteral collar comprising a vent configured to allow removal of fluid from the moat region; and
    a rotatable plug that reversibly seals the vent.

12. The syringe of claim 11, wherein the vent is configured to allow for removal of fluid between the enteral collar and the non-luer tip.

13. The syringe of claim 11, wherein the vent is rectangular, square, diamond, oval, or circular.

14. The syringe of claim 11, wherein the enteral collar comprises a number of vents in a range of from 4 to 12.

15. The syringe of claim 11, wherein the enteral collar comprises a plurality of vents equally spaced around a circumference of the enteral collar.

16. The syringe of claim 11, wherein the enteral collar is outside the fluid pathway and not in fluid communication with the chamber.

17. The syringe of claim 11, wherein the distal end of the enteral collar has an inner surface with threads for engaging a threaded, non-luer connector.

18. The syringe of claim 11, wherein the enteral collar is not removable or rotatable relative to the syringe barrel.

19. The syringe of claim 11, wherein the non-luer tip extends beyond the distal end of the enteral collar.

* * * * *